US012758514B2

(12) United States Patent
Nam

(10) Patent No.: US 12,758,514 B2

(45) Date of Patent: Oct. 13, 2026

(54) PHARMACEUTICAL COMPOSITION FOR TREATING ONYCHOMYCOSIS AND RELIEVING INGROWN TOENAIL PAIN

(71) Applicant: WOOSHIN LABOTTACH CO., LTD., Seoul (KR)

(72) Inventor: Taek Soo Nam, Seoul (KR)

(73) Assignee: WOOSHIN LABOTTACH CO., LTD., Seoul (KR)

( * ) Notice: Subject to any disclaimer, the term of this patent is extended or adjusted under 35 U.S.C. 154(b) by 547 days.

(21) Appl. No.: 18/136,313

(22) Filed: Apr. 18, 2023

(65) Prior Publication Data

US 2024/0238227 A1 Jul. 18, 2024

Related U.S. Application Data

(63) Continuation-in-part of application No. 18/096,028, filed on Jan. 12, 2023, now abandoned.

(51) Int. Cl.

| | |
|---|---|
| ***A61K 31/17*** | (2006.01) |
| ***A61K 9/70*** | (2006.01) |
| ***A61K 31/194*** | (2006.01) |
| ***A61K 31/4188*** | (2006.01) |
| ***A61K 47/32*** | (2006.01) |
| ***A61P 31/10*** | (2006.01) |

(52) U.S. Cl.

CPC ............ *A61K 31/17* (2013.01); *A61K 9/7023* (2013.01); *A61K 31/194* (2013.01); *A61K 31/4188* (2013.01); *A61K 47/32* (2013.01); *A61P 31/10* (2018.01)

(58) Field of Classification Search

CPC .... A61K 31/17; A61K 9/7023; A61K 31/194; A61K 31/4188; A61K 47/32; A61P 31/10

See application file for complete search history.

(56) References Cited

U.S. PATENT DOCUMENTS 5,525,635 A 6/1996 Moberg

FOREIGN PATENT DOCUMENTS

| | | | |
|---|---|---|---|
| EP | 3329910 A1 * | 6/2018 | |
| WO | 2014/140524 A1 | 9/2014 | |

OTHER PUBLICATIONS

Angelo et al.; Chemical and physical strategies in onychomycosis topical treatment: A review; Medical Mycology, 2017, 55, 461-475. (Year: 2017).*

Nail Fungus; Obtained from mayoclinic.org [Retrieved of Aug. 26, 2025] <URL: https://www.mayoclinic.org/diseases-conditions/nail-fungus/diagnosis-treatment/drc-20353300> (Year: 2024).*

(Continued)

*Primary Examiner* — Sarah Pihonak

*Assistant Examiner* — Jackson J Hernandez

(74) *Attorney, Agent, or Firm* — Revolution IP, PLLC

(57) ABSTRACT

A pharmaceutical composition in the form of a hydrogel for preventing or treating onychomycosis or relieving ingrown toenail pain, the pharmaceutical composition containing urea, biotin, fumaric acid, 1,3-butylene glycol, a gel-forming polymer, a crosslinking agent, and 45 to 60 wt % of water, and having keratolytic and moisture-retention abilities to provide a hydrated environment for fingernails, toenails and surrounding tissues.

1 Claim, 11 Drawing Sheets

(56) References Cited

OTHER PUBLICATIONS

Westerberg et al.; Onychomycosis: Current Trends in Diagnosis and Treatment; American Family Physician, 2013, 88, 762-770. (Year: 2013).*

Prevent; definition II.9.a of prevent, Oxford English Dictionary Online). Provided by the online dictionary at oed.com [retrieved on Mar. 5, 2025]. Retrieved from the Internet: <URL: https://www.oed.convdictionary/prevent_v?tl=true> (Year: 2007).*

Sparavigna et al.; Efficacy and tolerability of a biomineral formulation for treatment of onychoschizia: a randomized trial; Clinical, Cosmetic and Investigational Dermatology, 2019, 12, 355-362. (Year: 2019).*

Rothman et al.; What You Need to Know About Ingrown Toenail Fungus (Pain, Condition); Obtained from rothmanortho.com [retrieved on Jan. 2, 2026] <URL:https://rothmanortho.com/stories/blog/toe-nail-fungus>—Pub. Date: May 1, 2015.*

L. Emtestam et al., "Treatment of distal subungual onychomycosis with a topical preparation of urea, propylene glycol and lactic acid: results of a 24-week, double-blind, placebo-controlled study", Mycoses, Nov. 2012, vol. 55, Issue 6, pp. 532-540.

* cited by examiner

| | A | B | C | D | E | F | G | H | I | AVG | STDEV | RSD |
|---|---|---|---|---|---|---|---|---|---|---|---|---|
| Patch O | 2.27 | 1.79 | 1.75 | 1.23 | 2.11 | 1.53 | 2.14 | 1.18 | 1.93 | 1.77 | 0.3915 | 22% |
| Patch X | 2.35 | 1.05 | 1.09 | 0.71 | 2.06 | 1.29 | 1.49 | 0.86 | 1.39 | 1.37 | 0.5401 | 40% |

| | A | B | C | D | E | F | G | H | I | AVG | STDEV | RSD |
|---|---|---|---|---|---|---|---|---|---|---|---|---|
| Patch O | 1.98 | 1.57 | 0.88 | 1.1 | 2.55 | 0.63 | 1.01 | 0.91 | 0.35 | 1.22 | 0.6932 | 57% |
| Patch X | 0.81 | 1.19 | 0.25 | 0.6 | 2.06 | 0.37 | 0.97 | 0.42 | 0.31 | 0.7756 | 0.5783 | 75% |

PHARMACEUTICAL COMPOSITION FOR TREATING ONYCHOMYCOSIS AND RELIEVING INGROWN TOENAIL PAIN

BACKGROUND

1. Technical Field

The present invention relates to a pharmaceutical composition for preventing or treating onychomycosis and a method for preparing the same. More specifically, the present invention relates to a pharmaceutical composition in the form of a hydrogel for preventing or treating onychomycosis, the pharmaceutical composition containing urea, fumaric acid, and 1,3-butylene glycol as active ingredients and having keratolytic and moisture-retention abilities.

2. Related Art

Onychomycosis is a fungal infection of fingernails and/or toenails, which is caused mainly by infection with *Trichophyton rubrum, Trichophyton mentagrophytes*, and the like. Onychomycosis may be treated both systemically and topically. Antifungal agents such as terbinafine and itraconazole have been used for the systemic treatment of onychomycosis, but may cause side effects, including gastrointestinal side effects, headache, hepatotoxicity, and the like. For topical treatment of onychomycosis, lacquer formulations containing antifungal agents such as amorolfine, ciclopiroxolamine, or the like are used. The locker formulations may be applied directly to the infected sites and thus have the advantage of avoiding systemic exposure to the drug.

As a medicament for treating onychomycosis that does not contain an antifungal drug, a topical formulation in the form of lacquer containing urea, lactic acid, and propylene glycol has been developed (U.S. Pat. No. 5,525,635). The topical formulation in the form of lacquer is currently commercially available as commercial antifungal nail lacquer (Emtrix™) (OzHealth Pharma). Urea is known to have a nail dissolving effect. Lactic acid is used as an additive to dermatological products where it is included mainly for its exfoliating properties. In addition, propylene glycol is known to have not only keratolytic effects but also antibacterial and antimycotic properties. The mode of action of said topical formulation in the form of lacquer is not fully known, but may be mainly attributable to the osmotic effect of propylene glycol (L. Emtestam et al., Mycoses. 2012 November; 55 (6): 532-540). In addition, WO 2014/140524 discloses a formulation containing a triol such as glycerol and a base for adjusting the pH to 2 to 6, in order to improve the storage stability of the topical formulation in the form of lacquer disclosed in U.S. Pat. No. 5,525,635.

However, the known topical formulations for treating onychomycosis that does not contain an antifungal drug are in the form of lacquer, which makes it difficult to provide satisfactory keratolytic effects, and thus have limitations in exhibiting sufficient therapeutic activity.

SUMMARY

The present inventors have conducted various studies in order to develop an improved topical formulation for treating onychomycosis that contains no antifungal drug. In particular, the present inventors have conducted various studies in order to develop a formulation capable of exhibiting sufficient keratolytic effects. As a result, the present inventors have found that, when a high level of moisture content is maintained in the nail, drying phenomena in the nail may be prevented and active ingredients may easily penetrate the skin, thereby remarkably increasing the keratolytic effects. Particularly, the present inventors have found that, when urea in combination with a specific acid and diol compound, i.e., fumaric acid and 1,3-butylene glycol, is formulated in the form of a hydrogel having a water content of at least about 45%, the resulting formulation exhibits remarkably excellent keratolytic activity as well as remarkably increased moisture-retention ability (or moisture-maintenance ability).

Therefore, an object of the present invention is to provide a pharmaceutical composition in the form of a hydrogel for preventing or treating onychomycosis, the pharmaceutical composition containing urea, fumaric acid, and 1,3-butylene glycol and having keratolytic and moisture-retention abilities.

Another object of the present invention is to provide a method for preparing the pharmaceutical composition in the form of a hydrogel.

In accordance with one aspect of the present invention, there is provided a pharmaceutical composition in the form of a hydrogel for preventing or treating onychomycosis, the pharmaceutical composition containing urea, fumaric acid, 1,3-butylene glycol, a gel-forming polymer, a crosslinking agent, and 45 to 60 wt % of water, and having keratolytic and moisture-retention abilities. In addition, according to the present invention, it is possible to relieve ingrown toenail pain.

In one embodiment, the pharmaceutical composition of the present invention may contain 15 to 25 wt % of urea, 0.5 to 2.5 wt % of fumaric acid, 8 to 18 wt % of 1,3-butylene glycol, 5 to 10 wt % of the gel-forming polymer, 0.1 to 0.5 wt % of the crosslinking agent, and 45 to 60 wt % of water.

In accordance with another aspect of the present invention, there is provided a method for preparing a pharmaceutical composition for preventing or treating onychomycosis having keratolytic and moisture-retention abilities, the method comprising mixing urea, fumaric acid, 1,3-butylene glycol, a gel-forming polymer, a crosslinking agent, 45 to 60 wt % of water, and optionally at least one additive selected from the group consisting of a plasticizer, a thickener, a surfactant, a chelating agent and a preservative, to form a hydrogel. In addition, according to the present invention, it is possible to relieve ingrown toenail pain.

It has been found by the present invention that, when a high level of moisture content is maintained in the nail, drying phenomena in the nail may be prevented and active ingredients may easily penetrate the skin, thereby remarkably increasing the keratolytic effects. In particular, it has been found by the present invention that, when urea in combination with a specific acid and diol compound, i.e., fumaric acid and 1,3-butylene glycol, is formulated in the form of a hydrogel having a water content of at least about 45%, the resulting formulation exhibits remarkably excellent keratolytic activity as well as remarkably increased moisture-retention ability (or moisture-maintenance ability). Thus, the pharmaceutical composition in the form of a hydrogel according to the present invention has excellent keratolytic and moisture-retention abilities, and thus may be usefully applied for preventing or treating onychomycosis. In addition, according to the present invention, it is possible to relieve ingrown toenail pain.

BRIEF DESCRIPTION OF THE DRAWINGS

FIG. 1 shows the appearance of the toe before applying the patch, and FIGS. 2 to 5 show the appearances of the toe week 1, week 2, week 3 and week 4 after attachment of the patch, respectively.

FIG. 6 shows the appearance of the toe before applying the patch, and FIGS. 7 to 10 show the appearances of the toe at week 1, week 2, week 3 and week 4 after attachment of the patch, respectively.

FIG. 17 shows the toenail on day 1 of an ingrown toenail test, FIG. 18 shows the toenail into which the patch (Formulation Example 1) of the present invention has been inserted, FIG. 18 shows the toenail to which the patch of the present invention has been completely applied, and FIG. 20 shows that the ingrown toenail was relieved after 13 days.

DETAILED DESCRIPTION

Figure 1:
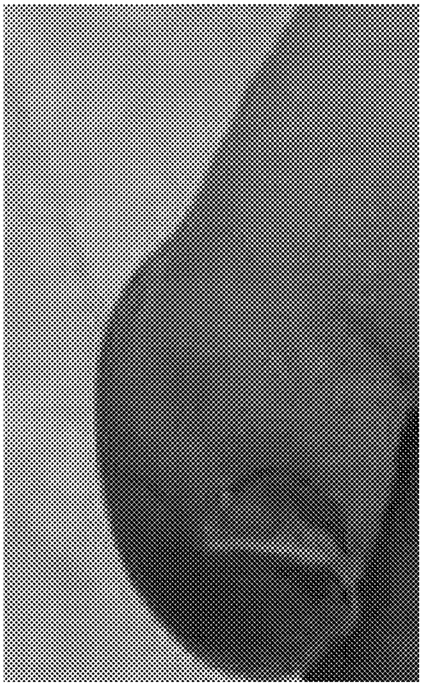
FIGS. 1 to 5 show the results of observing the toe after applying a patch prepared according to the present invention to an onychomycosis patient (42 years old, female). Specifically.
Figure 2:
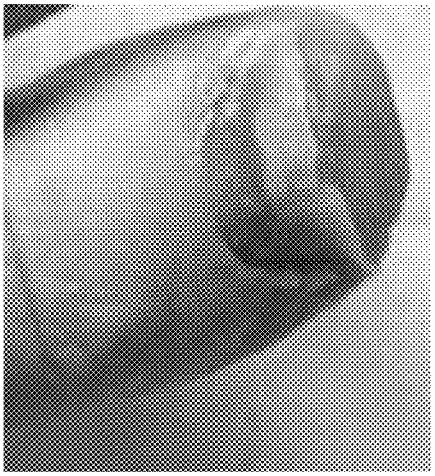
Figure 3:
Figure 4:
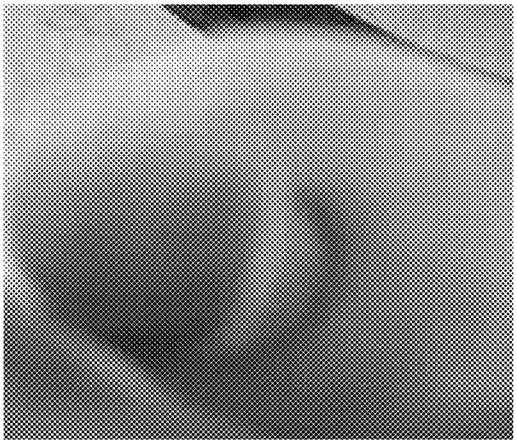
Figure 5:
Figure 6:
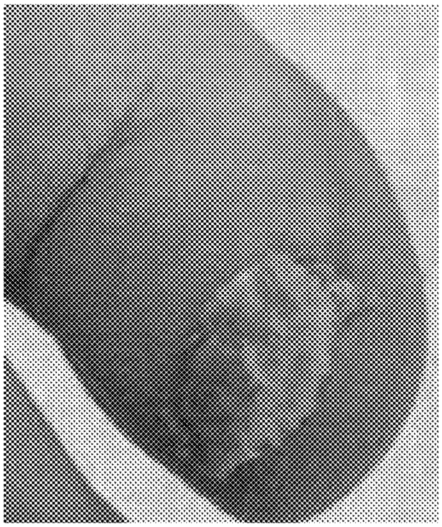
FIGS. 6 to 10 show the results of observing the toe after applying the patch prepared according to the present invention to an onychomycosis patient (35 years old, female). Specifically.
Figure 7:
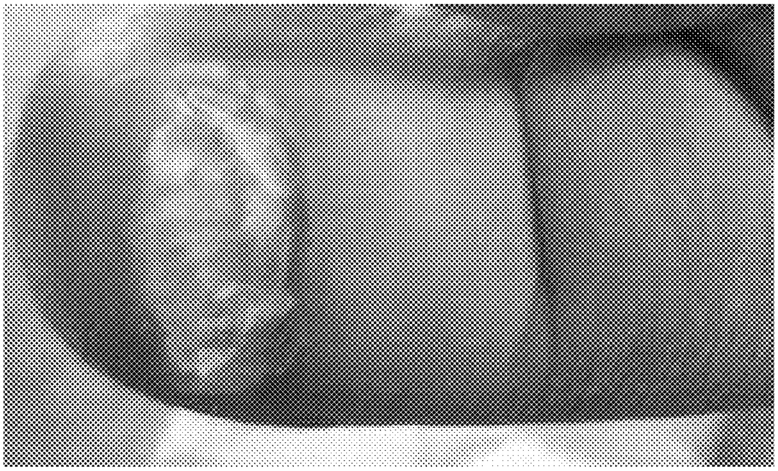
Figure 8:
Figure 9:
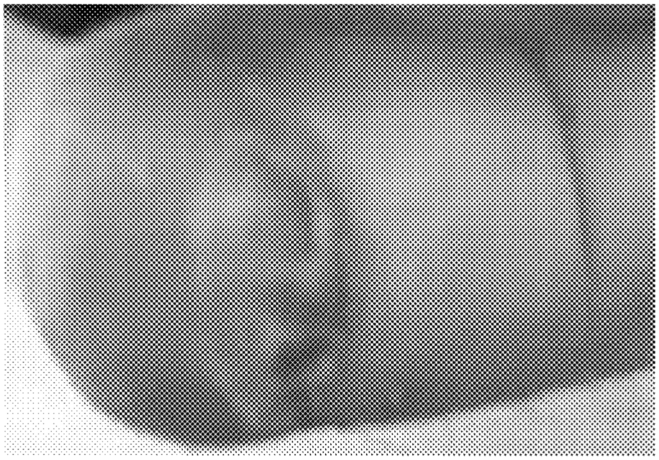
Figure 10:
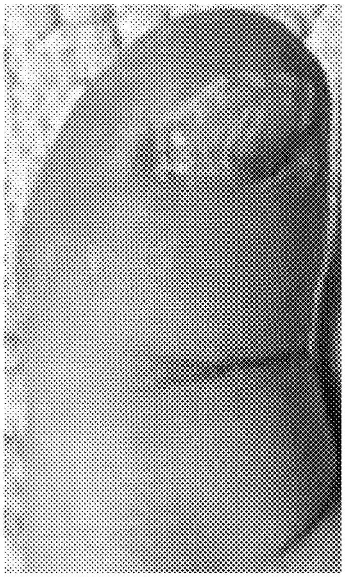
Figure 11:
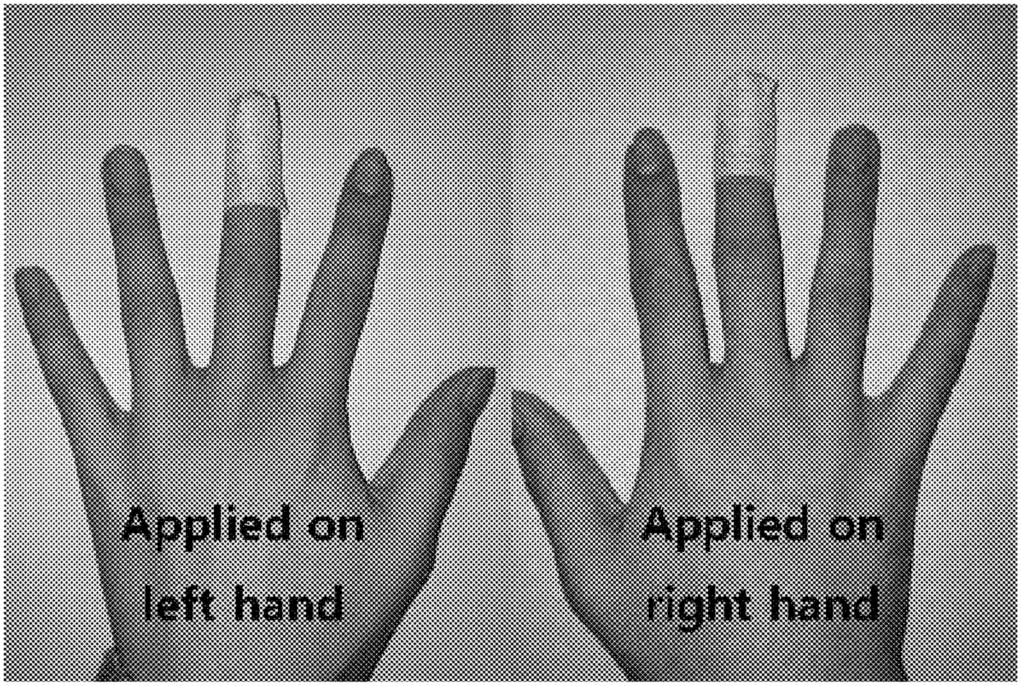
FIGS. 11 to 16 show the results of observing nail growth after applying the patch prepared according to the present invention.
Figure 12:
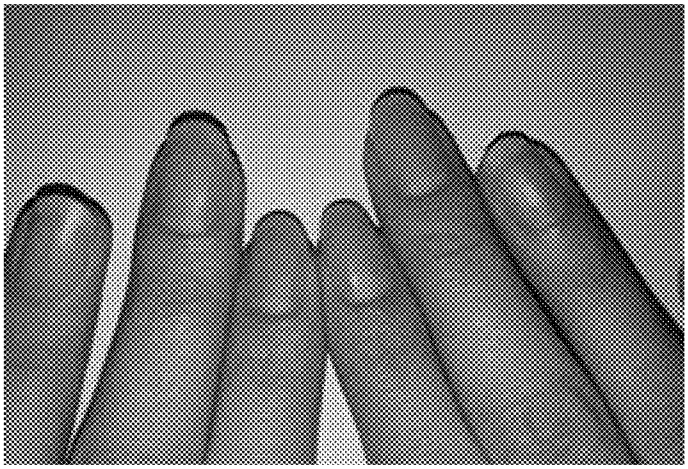
Figure 13:
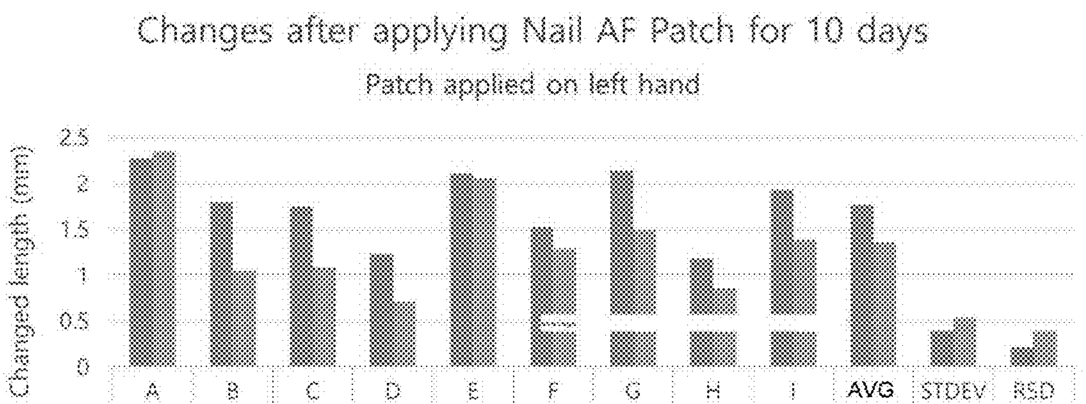
Figure 14:
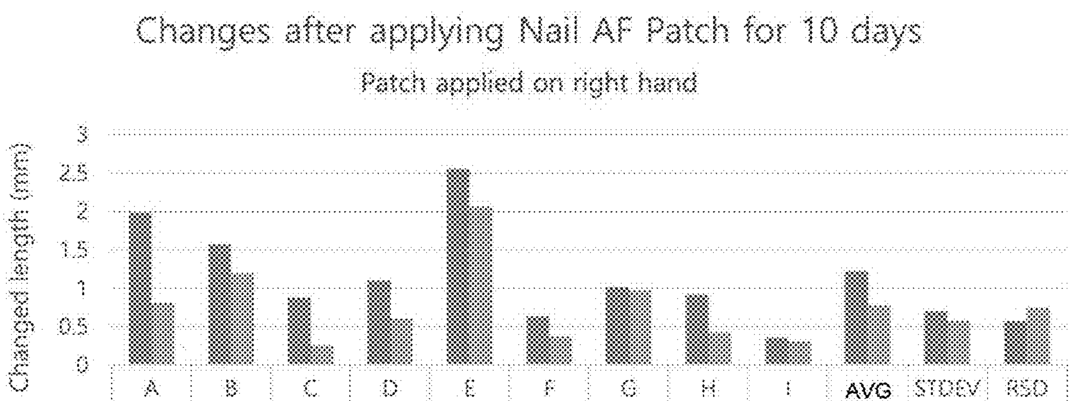
Figure 15:
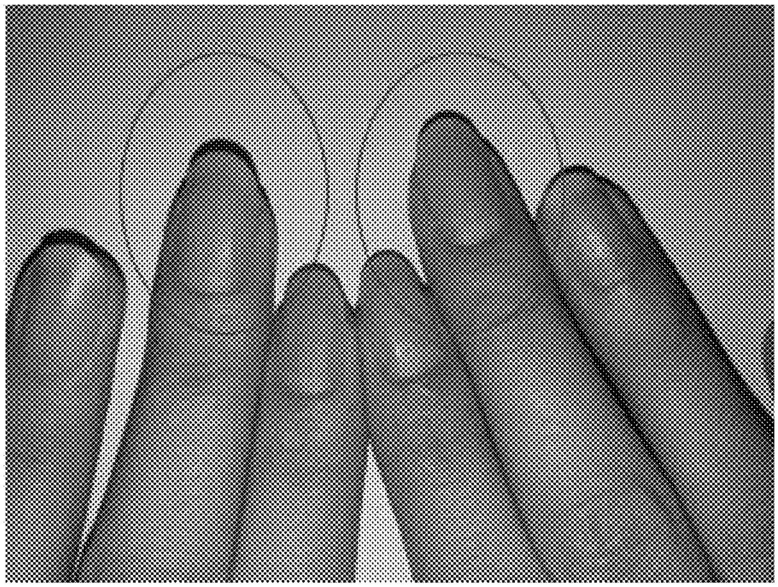
Figure 16:
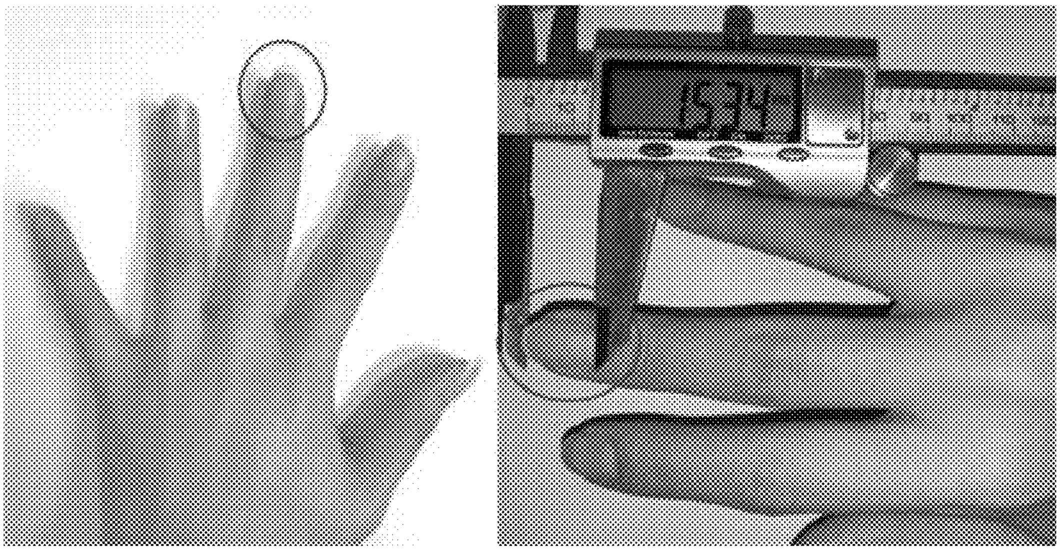
Figure 17:
FIGS. 17 to 20 show the results of observing whether an ingrown toenail was relieved after applying the patch (further including biotin) according to the present invention. Specifically.
Figure 18:
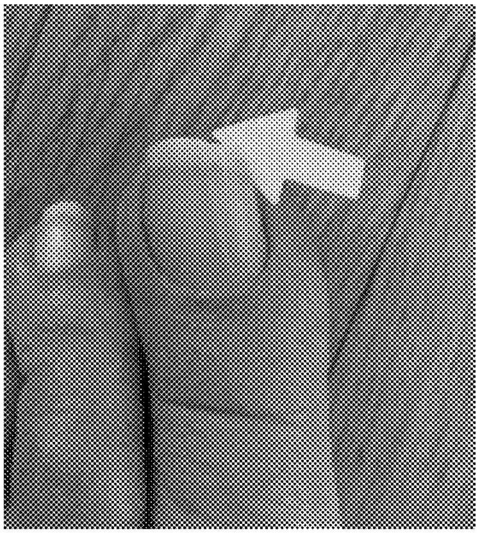
Figure 19:
Figure 20:
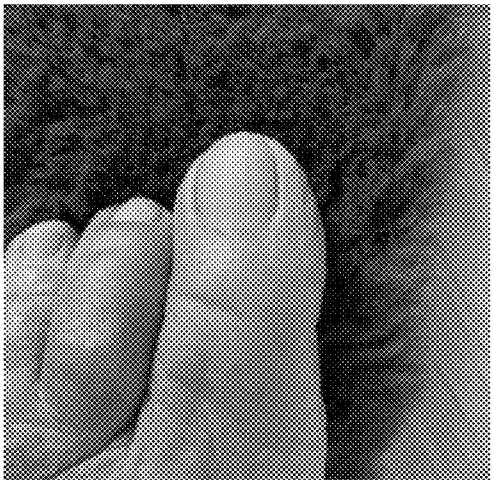

The present invention provides a pharmaceutical composition in the form of a hydrogel for preventing or treating onychomycosis, the pharmaceutical composition containing urea, fumaric acid, 1,3-butylene glycol, a gel-forming polymer, a crosslinking agent, and 45 to 60 wt % of water, and having keratolytic and moisture-retention abilities. In addition, according to the present invention, when the pharmaceutical composition further contains biotin, it may also relive ingrown toenail pain.

In the pharmaceutical composition of the present invention, the urea may be present in an amount of 15 to 25 wt %, preferably 18 to 23 wt %, more preferably about 20 wt %, based on the total weight of the composition. In addition, the fumaric acid may be present in an amount of 0.5 to 2.5 wt %, preferably 1.0 to 2.3 wt %, more preferably about 2.0 wt %, based on the total weight of the composition. The fumaric acid provides the viscosity suitable for forming a hydrogel, unlike other organic acids such as highly viscous and sticky lactic acid. Furthermore, the 1,3-butylene glycol may be present in an amount of 8 to 18 wt %, preferably 9 to 15 wt %, more preferably about 10 wt %, based on the total weight of the composition.

The pharmaceutical composition of the present invention contains a gel-forming polymer and a crosslinking agent for crosslinking the gel-forming polymer. The gel-forming polymer may be polyacrylic acid, a copolymer of acrylic acid and sodium acrylate, or a mixture thereof. The polyacrylic acid may be a polymer having a weight-average molecular weight of 100,000 to 400,000, preferably about 250,000. In addition, the copolymer of acrylic acid and sodium acrylate may be a copolymer having a weight-average molecular weight of 1,300,000 to 4,700,000, preferably about 3,000,000. More preferably, the copolymer may be a copolymer obtained by copolymerizing acrylic acid and sodium acrylate at a molar ratio of about 6:4. As the copolymer of acrylic acid and sodium acrylate, a commercially available copolymer of acrylic acid and sodium acrylate (AP-40F™) (Sumintomo Seika Chemicals Co., Ltd.) may also be used. The gel-forming polymer may be present in an amount sufficient for forming a hydrogel, for example in an amount of 5 to 10 wt %, preferably 6 wt %, based on the total weight of the composition. As the crosslinking agent, aluminum glycinate may be preferably used. The aluminum glycinate may be present in amount of 0.1 to 0.5 wt %, preferably about 0.2 wt %, based on the total weight of the composition.

In one embodiment, the pharmaceutical composition of the present invention may contain 15 to 25 wt % of urea, 0.5 to 2.5 wt % of fumaric acid, 8 to 18 wt % of 1,3-butylene glycol, 5 to 10 wt % of the gel-forming polymer, 0.1 to 0.5 wt % of the crosslinking agent, and 45 to 60 wt % of water.

The pharmaceutical composition of the present invention may contain a pharmaceutically acceptable additive that is commonly used in hydrogel formulations. For example, the pharmaceutical composition of the present invention may further contain at least one additive selected from the group consisting of a plasticizer, a thickener, a surfactant, a chelating agent and a preservative.

The plasticizer may comprise, for example, glycerin, and may be present in an amount of 3 to 8 wt % based on the total weight of the composition. The thickener may be at least one selected from the group consisting of carboxymethylcellulose or a salt thereof, polyvinylpyrrolidone, and polyvinyl alcohol, and may be present in an amount of 5 to 10 wt % based on the total weight of the composition. The surfactant may be at least one selected from the group consisting of sorbitan monooleate (for example, sorbitan monooleate (Span™ 80), etc.) and polyoxyethylene sorbitan fatty acid ester (for example, polysorbate 80 (Tween™ 80), etc.), and may be present in an amount of 0.3 to 1 wt % based on the total weight of the composition. The chelating agent may be ethylenediaminetetraacetic acid or its salt, and the preservative may be at least one selected from the group consisting of methylparaben and propylparaben. The contents of the chelating agent and the preservative are not specifically limited and may be appropriately selected by a person skilled in the art.

The present invention also provides a method for preparing the above-described pharmaceutical composition. That is, the present invention provides a method for preparing a pharmaceutical composition for preventing or treating onychomycosis having keratolytic and moisture-retention abilities, the method comprising mixing urea, fumaric acid, 1,3-butylene glycol, a gel-forming polymer, a crosslinking agent, 45 to 60 wt % of water, and optionally one or more excipients selected from the group consisting of a plasticizer, a thickener, a surfactant, a chelating agent and a preservative, to form a hydrogel. In addition, according to the present invention, when the pharmaceutical composition further contains biotin, it may also relive ingrown toenail pain.

Here, the urea, the fumaric acid, the 1,3-butylene glycol, the gel-forming polymer, the crosslinking agent, the plasticizer, the thickener, the surfactant, the chelating agent, and the preservative are as described above.

The mixing may be performed by mixing and stirring all the components at once under appropriate heating. In addition, the mixing may also be performed by preparing a plurality of mixed solutions containing some components and then mixing the mixed solutions. For example, the mixing may be performed by preparing an aqueous solution containing polyvinylpyrrolidone (aqueous solution A), preparing an aqueous solution containing polyvinyl alcohol (aqueous solution B), preparing an aqueous solution containing urea, biotin and fumaric acid (aqueous solution C), preparing a mixed solution of the remaining components, and then mixing aqueous solution A, aqueous solution B and aqueous solution C with the obtained mixed solution, followed by homogenization. The viscosity of the resulting hydrogel is preferably in the range of 100,000 to 2,000, 000 cps at 25° C.

In one embodiment of the preparation method of the present invention, based on the total weight of the composition, the urea may be used in an amount of 15 to 25 wt %; the fumaric acid may be used in an amount of 0.5 to 2.5 wt %; the 1,3-butylene glycol may be used in an amount of 8 to 18 wt %; the gel-forming polymer may be used in an amount of 5 to 10 wt %; the crosslinking agent may be used in an amount of 0.1 to 0.5 wt %; and the water may be used in an amount of 45 to 60 wt %.

The pharmaceutical composition of the present invention may be formulated in a form such as patch. For example, the pharmaceutical composition of the present invention may be formulated in a patch form by applying the hydrogel obtained according to the present invention onto a release layer and then forming a backing layer thereon. For the release layer, a conventional release liner or its laminate may be used. For example, it is possible to use a film of polyethylene terephthalate, cast polypropylene, silicone resin- or fluorine resin-coated polyethylene, polyester, polyvinyl chloride, polyvinylidene chloride, or the like, paper, or a laminate thereof. In addition, conventionally used non-drug-absorbable and flexible material may be used for the backing layer (also referred to as "backing membrane"). For example, for the backing layer, it is possible to use a non-woven fabric, a non-woven fabric coated with polyurethane, polyolefin, polyether, a multi-layer ethylene vinyl acetate film, polyester, polyurethane, or the like.

In the pharmaceutical composition obtained according to the present invention, for example, in the pharmaceutical composition in the form of a patch, the active ingredients, i.e., urea, fumaric acid, and 1,3-butylene glycol, may be applied in the amounts of 75 to 225 mg, 7.5 to 22.5 mg, and 37.5 to 112.5 mg per topical application, respectively, but the amounts may vary depending on patient conditions, attached sites, and the like. In addition, the pharmaceutical composition obtained according to the present invention, for example, the pharmaceutical composition in the form of a patch, may be applied topically once a day, without being limited thereto. The application may continue for at least one week, at least two weeks, at least three weeks, at least four weeks, and at least six weeks, while replacing with a new patch.

Hereinafter, the present invention will be described in more detail with reference to examples and test examples. These examples and test examples are for illustrating the present invention, and the scope of the present invention is not limited by these examples and test examples.

Formulation Examples: Preparation of Hydrogels and Patches Comprising the Same Hydrogels were prepared according to the components and contents shown in Table 1 below. The contents in Table 1 represent the wt % of each component in the hydrogel. Polyvinylpyrrolidone and polyvinyl alcohol were added to water (about 60% of the total weight of water used), and the resulting mixture was stirred while heating to 50° C. to obtain an aqueous solution (aqueous solution A). Urea and fumaric acid (tartaric acid in the case of Formulation Example 4) were added to the remaining amount of water, and the resulting mixture was stirred while heating to 80° C. to obtain an aqueous solution (aqueous solution B). 1,3-Butylene glycol, polyacrylic acid (AC-10LHPK™), a copolymer of acrylic acid and sodium acrylate (AP-40F™), aluminum glycinate, glycerin, sodium carboxymethylcellulose, sorbitan monooleate (Span™ 80), polysorbate 80 (Tween™ 80), sodium ethylenediaminetetraacetate, methylparaben, and propylparaben were homogeneously mixed to obtain a mixed solution. Aqueous solutions A and aqueous solution B were added to the mixed solution and then homogeneously mixed for about 15 minutes. The resulting mixed solution was applied onto an embossed polypropylene film, and then a non-woven fabric coated with polyurethane was laminated thereon to form a backing layer (backing membrane), thereby preparing hydrogel-containing formulations in the form of a patch.

TABLE 1

| | Formulation Example 1 | Formulation Example 2 | Formulation Example 3 | Formulation Example 4 | Range |
|---|---|---|---|---|---|
| Urea | 20.00 | 20.00 | — | 20.00 | 10 to 20 |
| Fumaric acid | 2.00 | 2.00 | 2.00 | — | 2 |
| Tartaric acid | — | — | — | 0.40 | 0.0 to 0.4 |
| Biotin | | | | | 0.1 |
| 1,3-bytylene glycol | 10.00 | 10.00 | 10.00 | 10.00 | 10 |
| Water | 50.23 | 35.23 | 50.23 | 50.23 | 30 to 50 |
| Polyacrylic acid | 2.00 | 2.00 | 2.00 | 2.00 | 2 |
| Copolymer of acrylic acid and sodium acrylate | 4.00 | 4.00 | 4.00 | 4.00 | 4 |
| Aluminum glycinate | 0.20 | 0.20 | 0.20 | 0.20 | 0.2 |
| Glycerin | 5.00 | 20.00 | 25.00 | 6.60 | 10 to 30 |
| Sodium carboxymethylcellulose | 2.50 | 2.50 | 2.50 | 2.50 | 2.5 |
| Polyvinylpyrrolidone | 0.80 | 0.80 | 0.80 | 0.80 | 0.8 |
| Polyvinyl alcohol | 2.50 | 2.50 | 2.50 | 2.50 | 2.5 |
| sorbitan monooleate (Span ™ 80) | 0.25 | 0.25 | 0.25 | 0.25 | 0.25 |
| polysorbate 80 (Tween ™ 80) | 0.25 | 0.25 | 0.25 | 0.25 | 0.25 |
| Sodium ethylenediaminetetraacetate | 0.12 | 0.12 | 0.12 | 0.12 | 0.12 |
| Methylparaben | 0.10 | 0.10 | 0.10 | 0.10 | 0.1 |
| Propylparaben | 0.05 | 0.05 | 0.05 | 0.05 | 0.05 |
| Sum | 100.00 | 100.00 | 100.00 | 100.00 | 100 |

Experimental Example 1: Assessment of Keratolytic and Moisture-Retention Abilities Each of the patches obtained in Formulation Examples 1 to 4 and the lacquer formulation commercial antifungal nail lacquer (Emtrix™) (OzHealth Pharma) was attached to the pig's toenail for 5 hours, and then the keratolytic and moisture-retention abilities of each patch were assessed. Assessment of the moisture-retention ability was performed by measuring the swelling caused by the retention of moisture therein. Namely, assessment of the moisture-retention ability was performed by measuring the toenail thickness changes before and after application of each formulation. Assessment of the keratolytic effect was performed by measuring the toenail hardness changes before and after application of each formulation using a texture analyzer. When the thickness and the hardness before application of each formulation were each taken as 100%, the changes in the thickness and the hardness after application of each formulation are shown in Tables 2 and 3 below.

TABLE 2

| | Formulation Example 1 | Formulation Example 2 | Formulation Example 3 | Formulation Example 4 | Commercial antifungal nail lacquer (Emtrix ™) |
|---|---|---|---|---|---|
| Thickness after application | 114.01% | 102.41% | 94.20% | 95.25% | 96.92% |
| Amount changed | 14.01% | 2.41% | −5.80% | −4.75% | −3.08% |

TABLE 3

| | Formulation Example 1 | Formulation Example 2 | Formulation Example 3 | Formulation Example 4 | Commercial antifungal nail lacquer (Emtrix ™) |
|---|---|---|---|---|---|
| Hardness after application | 78.96% | 99.70% | 86.93% | 84.01% | 99.28% |
| Amount changed | −21.04% | −0.30% | −13.07% | −15.99% | −0.72% |

As can be seen from the results in Table 2 above, the hydrogel formulation of Formulation Example 1 exhibited excellent moisture-retention ability. On the contrary, the formulations containing no urea or containing no fumaric acid (i.e., Formulation Examples 3 and 4) and the formulation in the form of lacquer (commercial antifungal nail lacquer (Emtrix™)) did not exhibit moisture-retention ability, and the formulation having a water content of about 35% (i.e., Formulation Example 2) also did not exhibit significant moisture-retention ability.

In addition, as can be seen from the results in Table 3 above, the hydrogel formulations exhibited relatively excellent keratolytic effects compared to the formulation in the form of lacquer (commercial antifungal nail lacquer (Emtrix™)), and the formulation of Formulation Example 1 containing fumaric acid exhibited the best keratolytic effect.

Test Example 2: Clinical Assessment

The patch obtained in Formulation Example 1 was subjected to clinical trials on onychomycosis patients.

The patch of Formulation Example 1 was applied to an onychomycosis patient (42 years old, female), who was resistant to 1% itraconazole cream (Sporanox™). The patch was attached to the big toe of the left foot for 24 hours, and then replaced with a new patch every day. The toe was photographed before application of the patch (FIG. 1) and one week (FIG. 2), two weeks (FIG. 3), three weeks (FIG. 4) and four weeks (FIG. 5) after application of the patch, and the results are shown in FIGS. 1 to 5.

In addition, the patch of Formulation Example 1 was applied to an onychomycosis patient (35 years old, female), who was resistant to both skin external preparations and oral preparations. The patch was attached to the big toe of the left foot for 24 hours, and then replaced with a new patch every day. The toe was photographed before application of the patch (FIG. 6) and one week (FIG. 7), two weeks (FIG. 8), three weeks (FIG. 9) and four weeks (FIG. 10) after application of the patch, and the results are shown in FIGS. 6 to 10.

From the results in FIGS. 1 to 10, it can be seen that the patch obtained according to the present invention has an excellent therapeutic activity against onychomycosis.

Test Example 3: Assessment of Nail Growth

On nine male and female adults between the ages of 20 and 50, a test for the nail growth enhancing efficacy of the test product was performed by measuring the lengths of the middle fingernails of both hands with Vernier calipers before the use of the product and after 11-day use of the product.

TABLE 4

Figure 21:
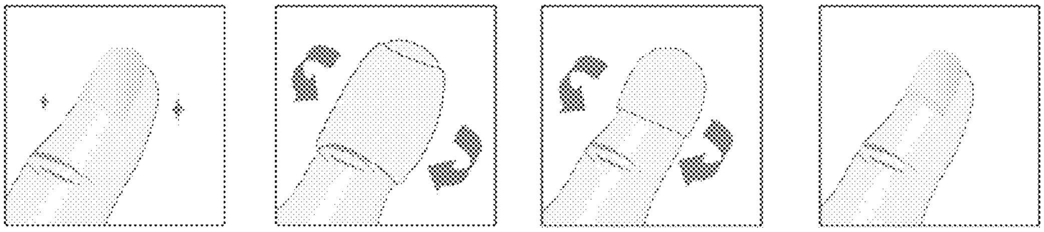
FIG. 21 is a diagram illustrating a patch application method in Example 3.

| | Formulation Example 1 |
|---|---|
| Active ingredients | Urea, 1,3-butylene glycol, and fumaric acid |
| Product feature | Patch having hydrogel applied thereto |
| Application area | On the nail |
| Application method | After the inner release liner is removed according to the shape of each nail, the patch is attached to cover the entire finger and detached after about 8 hours as shown in FIG. 21. |

Instrumental measurement and assessment were conducted in a place where the test subject was maintained under constant temperature and humidity conditions (temperature: 22±3° C., and humidity: 25±5%), and the lengths of the middle fingernails of the left and right hands were measured with Vernier calipers. For measurement, the lengths of the middle fingernails of both hands were measured before and after the use of the product.

FIG. 1. The Middle Finger which is the Measurement Site

Vernier calipers are instruments capable of simple and precise measurements without numerical fluctuations and errors. In this test, the length of the length of each middle fingernail was measured before and after the use of the product, and the change in the fingernail length was analyzed. The length from the tip of the nail to the tip of the cuticle was measured, and measurement values (mm) were obtained.

The results obtained through instrumental assessment were statistically analyzed for significance through a paired t-test, and measured values were expressed as mean values.

This test was conducted on 9 healthy adults who met the test subject exclusion criteria and selection criteria, and all the test subjects faithfully performed the entire test process according to the protocol.

When comparing before the use of the test product and after 11-day use of the test product, it was confirmed that the test product significantly enhanced nail growth.

TABLE 5

Vernier calipers measurements (after attachment of patch to left-hand middle fingernail)

| Test subject | Before patch attachment (Jan. 17, 20xx) (unit: mm) | | After patch attachment (Jan. 28, 20xx) (unit: mm) | |
|---|---|---|---|---|
| | Left hand | Right hand | Left hand | Right hand |
| A | 13.36 | 12.52 | 14.63 | 14.87 |
| B | 9.38 | 10.52 | 11.17 | 11.57 |
| C | 10.12 | 11.02 | 11.87 | 12.11 |
| D | 15.42 | 13.79 | 16.65 | 15.5 |
| E | 13.74 | 12.65 | 15.75 | 14.71 |
| F | 17.68 | 17.3 | 19.21 | 18.59 |
| G | 11.7 | 12.77 | 13.84 | 14.26 |
| H | 14.6 | 15.24 | 15.78 | 16.1 |
| I | 9.08 | 9.68 | 11.01 | 11.07 |

t = 4.2102, p-value = 0.002955

TABLE 6

Vernier calipers measurements (after attachment of patch to right-hand middle fingernail)

| Test subject | Before patch attachment (Feb. 13, 20xx) (unit: mm) | | After patch attachment (Feb. 24, 20xx) (unit: mm) | |
|---|---|---|---|---|
| | Left hand | Right hand | Left hand | Right hand |
| A | 14.19 | 14.23 | 15 | 16.21 |
| B | 10.12 | 9.85 | 11.31 | 11.42 |
| C | 10.9 | 11.37 | 11.15 | 12.25 |
| D | 13.41 | 13.3 | 14.01 | 14.4 |
| E | 13.53 | 13.24 | 15.59 | 15.79 |
| F | 16.73 | 17.12 | 17.1 | 17.75 |
| G | 12.08 | 13.06 | 13.05 | 14.07 |
| H | 14.72 | 16.26 | 15.14 | 17.17 |
| I | 11.24 | 11.25 | 11.55 | 11.6 |

t=3.903, p-value=0.004523

When the case of attaching the patch to the right hand and the case of attaching the patch to the left hand were integrated, the t-test value and the p-value were calculated as t_total=5.861 and p-value_total=0.0000189.

The results of the subjective survey answered by all test subjects through the questionnaire during the test are as follows.

TABLE 7

Survey results after using test product (n = 9)

| Item | Number of test subjects who gave positive answer | Satisfaction (5-point scale) |
|---|---|---|
| The nail surface seems to have been smoother | 9 | 5 |
| It seems that dryness has decreased and nail splitting has been alleviated | 9 | 4 |
| The cuticle around the nail seems to have been tidied up | 9 | 5 |
| Nail seems to grow fast | 9 | 4 |

(5-point scale: 1. Not at all/ 2. Slightly/ 3. Moderately/ 4. Very/ 5. Extremely)

This test was conducted to assess the nail growth enhancing efficacy of the formulation of Formulation Example 1 developed by Wooshin Labottach Co. Ltd.

As a result of instrumental measurement, it was confirmed that the growth rate of the left-hand middle fingernail, to which the patch of the present invention was attached, increased by 0.5 mm on average over 11 days, which corresponded to about 130% of the nail growth rate before attachment of the patch (a significant level of p-value=0.002955).

As a result of attaching the patch of the present invention to the middle fingernail of the right hand after about 2 weeks and measuring the change in the fingernail length, it was confirmed that the growth rate of the middle fingernail of the right hand, to which the nail patch of the present invention was attached, increased by 0.44 mm on average over 11 days, which corresponded to about 131.2% of the nail growth rate before attachment of the patch (a significant level of p-value=0.004523).

Therefore, as a result of assessing the nail growth promoting or stimulating efficacy of the nail patch of the present invention, it is considered that, when the patched is attached for about 8 hours or more per day for 11 days, it helps nails grow faster with a significance of p-value=$1.89\times10^{-5}$ for the result values for the left and right hand fingernails.

In addition to the above results, the nail growth promoting or stimulating effect of the nail patch of the present invention is considered to help nails grow faster in both women and men, both left-handers and right-handers, and all age groups.

Probable mechanisms for these results are as follows:

1) A hydrated environment of the nail and surrounding tissue, which results from hydration of the hydrogel coating of the nail;
2) Increased permeability and supply of nutrients and oxygen from blood vessels, and inhibition of nail deformation by continuous hydration of nails; and
3) Sterilization and microbial growth prevention (e.g., prevention of onychomycosis) as a result of cell debris adsorption.

Test Example 4: Effect on Relief of Ingrown Toenail Pain

The test subject (comprising biotin) had been changing the product once, sometimes twice a day. The test subject has made a complete recovery, the nail is of appropriate shape, no growing into the surrounding tissue, no pain or signs of inflammation. During the study the test subject was able to walk normally and was able to wear normal footwear.

The test subject reports of being satisfied with the result, felt immediate relief a few hours after insertion of the product. The test subject was able to walk and move around normally the entire time.

Ingrown nail on left big toe, with acute inflammation of the surrounding tissue, moderate pain (FIGS. 17 to 20).

Day 0: Receives the product. Is shown how to properly insert the product in detail.

Day 1: After inserting the product the patient notices the pain is gone. The product is inserted without any problems.

Day 2 and onwards: Without pain, visible improvement of the condition.

Day 13: Complete recovery, the test subject is without pain, no signs of inflammation.

What is claimed is:

1. A method of treating onychomycosis or relieving ingrown toenail pain while enhancing nail growth in a subject, comprising:

topically administering to a fingernail or toenail of the subject a pharmaceutical composition in the form of a hydrogel patch, wherein the hydrogel patch comprises:

a release layer;

a hydrogel layer disposed on the release layer; and a backing layer laminated on the hydrogel layer, the backing layer comprising a non-woven fabric coated with polyurethane, wherein the hydrogel layer has a viscosity of 100,000 to 2,000,000 cps at 25° C., and comprises, based on a total weight of the hydrogel layer;

10 to 20 wt % of urea;

1 to 2.3 wt % of fumaric acid;

0.1 wt % of biotin;

9 to 15 wt % of 1,3-butylene glycol;

5 to 10 wt % of a gel-forming polymer, wherein the gel-forming polymer comprises polyacrylic acid, a copolymer of acrylic acid and sodium acrylate, or a mixture of polyacrylic acid and the copolymer of acrylic acid and sodium acrylate;

0.1 to 0.5 wt % of a crosslinking agent; and 45 to 60 wt % of water, wherein the pharmaceutical composition has keratolytic and moisture-retention abilities to provide a hydrated environment for fingernails, toenails, and surrounding tissues.

* * * * *